United States Patent [19]

Penniman

[11] Patent Number: 5,365,775
[45] Date of Patent: Nov. 22, 1994

[54] PROCESS FOR AUTOMATIC MEASUREMENT OF SPECIFIC FILTRATION RESISTANCE AND ELECTROSTATIC CHARGE OF A FIBROUS DISPERSION

[76] Inventor: John G. Penniman, P.O. Box 930, Carmel, N.Y. 10512

[21] Appl. No.: 127,007

[22] Filed: Sep. 27, 1993

[51] Int. Cl.⁵ .................... G01N 11/02; G01N 33/84; D21C 1/10
[52] U.S. Cl. ........................ 73/53.04; 73/53.03; 73/61.73; 73/61.63; 162/198; 162/263; 324/71.1; 324/348
[58] Field of Search ............ 73/53.04, 53.03, 61.63, 73/61.73; 324/353, 71.1, 348; 162/198, 263

[56] References Cited

U.S. PATENT DOCUMENTS

| | | | |
|---|---|---|---|
| 2,550,005 | 4/1951 | Doll | 324/351 |
| 2,569,625 | 10/1951 | Wyllie | 324/351 |
| 3,802,964 | 4/1974 | Forgacs et al. | 162/263 |
| 4,274,937 | 6/1981 | Findl et al. | 204/195 R |
| 4,427,944 | 1/1984 | Chandler | 324/353 |
| 4,433,299 | 2/1984 | Kawai et al. | 324/71.1 |
| 4,535,285 | 8/1985 | Evans et al. | 324/71.1 |
| 4,552,019 | 11/1985 | Freeman | 162/198 |
| 4,687,986 | 8/1987 | Eriksson | 73/53.04 |
| 4,755,305 | 6/1988 | Fremont et al. | 210/748 |
| 4,969,351 | 11/1990 | Halley et al. | 73/53.04 |

FOREIGN PATENT DOCUMENTS

| | | | |
|---|---|---|---|
| 0271430 | 9/1989 | Germany | 73/53.03 |
| 0272508 | 10/1989 | Germany | 73/53.03 |
| 0583227 | 12/1977 | U.S.S.R. | 73/53.03 |

Primary Examiner—Thomas P. Noland
Assistant Examiner—J. David Wiggins
Attorney, Agent, or Firm—William R. Moran

[57] ABSTRACT

A method is provided to monitor specific filtration resistance, total drainage resistance and drainage flow rate in a continuous on-line manner in the paper making process. It can be combined with the simultaneous measurement of streaming potential or zeta potential so as to enable optimization of the chemistry of the papermaking process.

18 Claims, 14 Drawing Sheets

```
ZETADUMP printout of ZETADATA log file 060392B.LOG

#   Fill time  Chamber  Rinse Time  Rinse  Interval  Log File Type
1     12.0      0.686        2         0             13:34:13

#    ZETA RANGE   COND TEMP DRAIN  CONF LOG File Type 5
1   -7.25 0.00    320 17.9 26.8   0.998 12:34:14
1   -6.95 0.00    326 16.9 28.0   0.975 12:35:31
1   -7.17 0.00    329 16.9 28.0   0.985 12:36:47
1   -7.21 0.00    329 16.9 27.8   0.980 12:38:03
1   -7.22 0.00    331 17.1 27.8   0.981 12:39:19
1   -7.49 0.00    334 17.1 28.1   0.987 12:40:35
1   -7.21 0.00    332 17.3 27.9   0.979 12:41:51
1   -7.37 0.00    332 17.3 28.6   0.979 12:43:07
1   -7.21 0.00    332 17.3 27.7   0.980 12:44:23
1   -7.26 0.00    327 17.3 28.0   0.984 12:45:39
1   -7.47 0.00    327 27.5 27.8   0.984 12:46:55
1   -7.67 0.00    336 17.5 28.4   0.991 12:48:11
1   -7.39 0.00    334 17.5 29.0   0.982 12:49:27

OPERATOR COMMENT Log File Type 3
    ADD 0.25% NALCO 7607

#    ZETA RANGE   COND TEMP DRAIN  CONF LOG File Type 5
1   -7.42 0.00    335 17.7 29.0   0.981 12:50:43
1   12.54 0.00    334 17.5 29.6   0.987 12:52:22
1    7.11 0.00    332 17.7 28.1   0.984 12:53:38
1    5.40 0.00    336 17.7 29.0   0.991 12:54:54
1    4.87 0.00    327 17.7 27.0   0.982 12:56:12
1    3.94 0.00    331 17.7 27.1   0.992 12:57:28
1    3.80 0.00    322 18.1 27.3   0.984 12:58:45
1    3.21 0.00    301 17.9 29.0   0.982 12:00:00

OPERATOR COMMENT Log File Type 3
    ADD 1% BENTONITE                         13:02:31  6/03/92

#    ZETA RANGE   COND TEMP DRAIN  CONF LOG File Type 5
1    3.12 0.00    310 17.9 27.7   0.984 13:01:18
1   -5.44 0.00    340 17.9 40.5   0.985 13:02:50
1   -3.25 0.00    339 17.9 33.9   0.987 13:04:07
1   -2.86 0.00    322 18.1 32.2   0.989 13:05:23
1   -3.19 0.00    339 18.3 31.1   0.991 13:06:40
1   -2.80 0.00    340 18.3 30.4   0.981 13:07:57
1   -2.74 0.00    333 18.3 29.5   0.982 13:09:14
1   -3.22 0.00    338 18.3 30.1   0.985 13:10:31
1   -3.01 0.00    316 18.3 28.4   0.987 13:11:48
1   -3.38 0.00    336 18.5 29.6   0.987 13:13:05
1   -3.35 0.00    333 18.5 28.8   0.990 13:14:21
```

FIG. 11

PROCESS FOR AUTOMATIC MEASUREMENT OF SPECIFIC FILTRATION RESISTANCE AND ELECTROSTATIC CHARGE OF A FIBROUS DISPERSION

BACKGROUND OF THE INVENTION

1) Field of the Invention

This invention relates in general to the paper making industry. In one aspect, the invention relates to a method for monitoring specific filtration resistance in a continuous on-line manner. In another aspect, the invention relates to a method for monitoring streaming potential and specific filtration resistance simultaneously in a continuous on-line manner. In a further aspect the invention is directed to a method for predicting drainage on the paper machine.

2) Background Art

Paper makers have known for a long time that the paper machine is a dynamic changing system. It gives the illusion of being a steady state process but when closely examined from a water quality perspective, the water quality is always slowly changing. The reason for this is the long times to equilibrium because of the high residence time recycle loops in the process. Much fundamental understanding exists about retention and drainage on the paper machine but attempts in practical application have been unsuccessful because of the changing system. A fundamental property which is important to retention on the paper machine is the state of the charge on the fiber surface, and a fundamental property important to drainage is specific filtration resistance, hereinafter also referred to as SFR.

The trend has been away from laboratory measurements and toward on-line continuous measurements for both drainage and electrostatic charge.

Zeta potential is an electrokinetic property of particles suspended in an aqueous medium containing charged ionic species and is an expression of the charge developed en or adjacent to such particles. It has been recognized that the zeta potential of fibrous particles in the feed stock or furnish, used in paper making, has a considerable influence upon the paper produced therefrom. Zeta potential cannot be measured directly; however, it can be calculated from measurements of a related parameter known as streaming potential.

A general discussion of zeta potential and its relevance to paper making is provided in "Electro kinetics in Paper Making—a position paper" by R. A. Stratton and J. W. Swanson in TAPPI, 64 No. 1, page 79-83 (1981). A survey of various methods of measuring zeta potential, including those reliant upon measurements of streaming potential, is given in an article by H. J. Jacobson et al, in Colloid and Polymer Science 263; 3-24 (1985).

From these references, it can be seen that the zeta potential of feed stock or furnish, exiting the head box of a paper making machine, influences the quality of the paper produced by the machine, as a result of its significant effect during paper formation on the wire of the machine. It is known that, in principle, a high particle charge is necessary to ionically stabilize colloidal emulsions or dispersions. There is a mutual repulsion between charged particles of the same polarity which keeps the particles apart and thereby imparts stability to an emulsion or dispersion system. Thus, stable dispersions of clay, calcium carbonate or titanium dioxide can have a charge or zeta potential of $-50$ to $-60$ mV. or even higher. Cellulose pulp dispersions typically have a zeta potential in the range of $-15$ to $-20$ mV. Cationic charge neutralizing chemicals such as alum, quaternary amines and wet strength resins, can reduce the zeta potential of a paper making furnish to within the range of 0 to $-8$ mV. At these low values, the repulsive effect of the charge on the suspended particles is reduced to a negligible value and coagulation is maximized. Conversely, at higher zeta potentials the degree of coagulation is reduced as the repulsive effect is increased. Thus, properties such as first pass retention, formation, drainage, white water consistency and strength can be optimized for a particular type of paper by adjusting the zeta potential of its precursor furnish to an optimum. Early attempts to apply zeta potential technology were often unsuccessful because the system conditions were different by the time the measurement was taken in the laboratory. This difficulty led to the development of the Zeta Data TM on-line streaming potential instrument. It was the first commercially available on-line streaming potential device.

In the drainage measurement field a similar evolution has taken place. The standard of the industry to measure drainage is Canadian Standard Freeness (CSF) in North America, or Schopper Riegler Freeness (SR) in Europe. They are empirical tests which measure the drainage time of a fixed volume of a sample. They give a qualitative picture of how a stock drains but no theory exists which can extrapolate their values to drainage on the paper machine. The fundamental measurement which characterizes stock drainage and has a theoretical underpinning is specific filtration resistance.

Specific filtration resistance is a property of the slurry and the conditions under which the pad is formed. It is a basic inherent property of material being drained.

The idea to use SFR to characterize stock drainage was introduce in the 1950's by Ingmanson and refined into a workable concept by Springer and Pires in 1989. The concept is good enough to be used to predict drainage down a paper machine. With such a parameter as specific filtration resistance available, the paper industry can phase out it's dependence on Freeness. The need for on-line Freeness testing was acknowledged in that several companies market such devices which have had significant commercial acceptance. Specific filtration resistance was not used due to industry lack of familiarity with the theory because user-friendly apparatus did not exist.

It is evident from the foregoing that there is a need for a method which allows substantially continuous and accurate monitoring of the specific filtration resistance of paper making feed stock or furnish.

The paper maker should be able to tell the drainage of the stock prior to entering the head box and adjust the electrochemical conditions with an appropriate polymer if there are going to be drainage problems which would slow down the machine. The device would be useful for monitoring and controlling refining conditions. The instrument should be very useful for monitoring the new microparticulate techniques which are aimed at maximization of retention, drainage and formation. It is therefore an object of the invention to provide a method for monitoring specific filtration resistance in paper making feed stock or furnish. Another object of this invention is to provide a method for the continuous, simultaneous and accurate monitoring of streaming potential and specific filtration resistance of a primarily fibrous material in a fluid. A further object is to provide a method for the determination of specific filtration resistance in furnish in order to predict drainage characteristics and thereby be enabled to make appropriate changes in the physical or chemical composition of the furnish either by refining or the addition of chemicals. These and other objects will readily become apparent to those skilled in the art in the light of the teachings herein set forth.

SUMMARY OF THE INVENTION

In its broad aspect, the present invention is directed to a method for the continuous and accurate monitoring of the specific filtration resistance or the simultaneous monitoring of both the streaming potential and specific filtration resistance of a fibrous dispersion in a fluid. The method comprises passing the fluid through a screen until a pad of the solid material is formed on the screen, maintaining the pressure on the screen side of the pad at a known value with respect to the pressure on the opposing side of the pad, measuring the temperature of the fluid, measuring the height of the liquid interface on the screen side of the pad, and calculating the specific filtration resistance or simultaneously calculating both the streaming potential and specific filtration resistance from the measurements taken.

The procedure of determining SFR and/or both SFR and streaming potential simultaneously is a breakthrough and is believed to be novel.

DESCRIPTION OF THE DRAWINGS

FIGS. 9–12 represent printouts of drainage and zeta potential graphs, their overlay and logfile.

DESCRIPTION OF THE PREFERRED EMBODIMENTS

Figure 1:
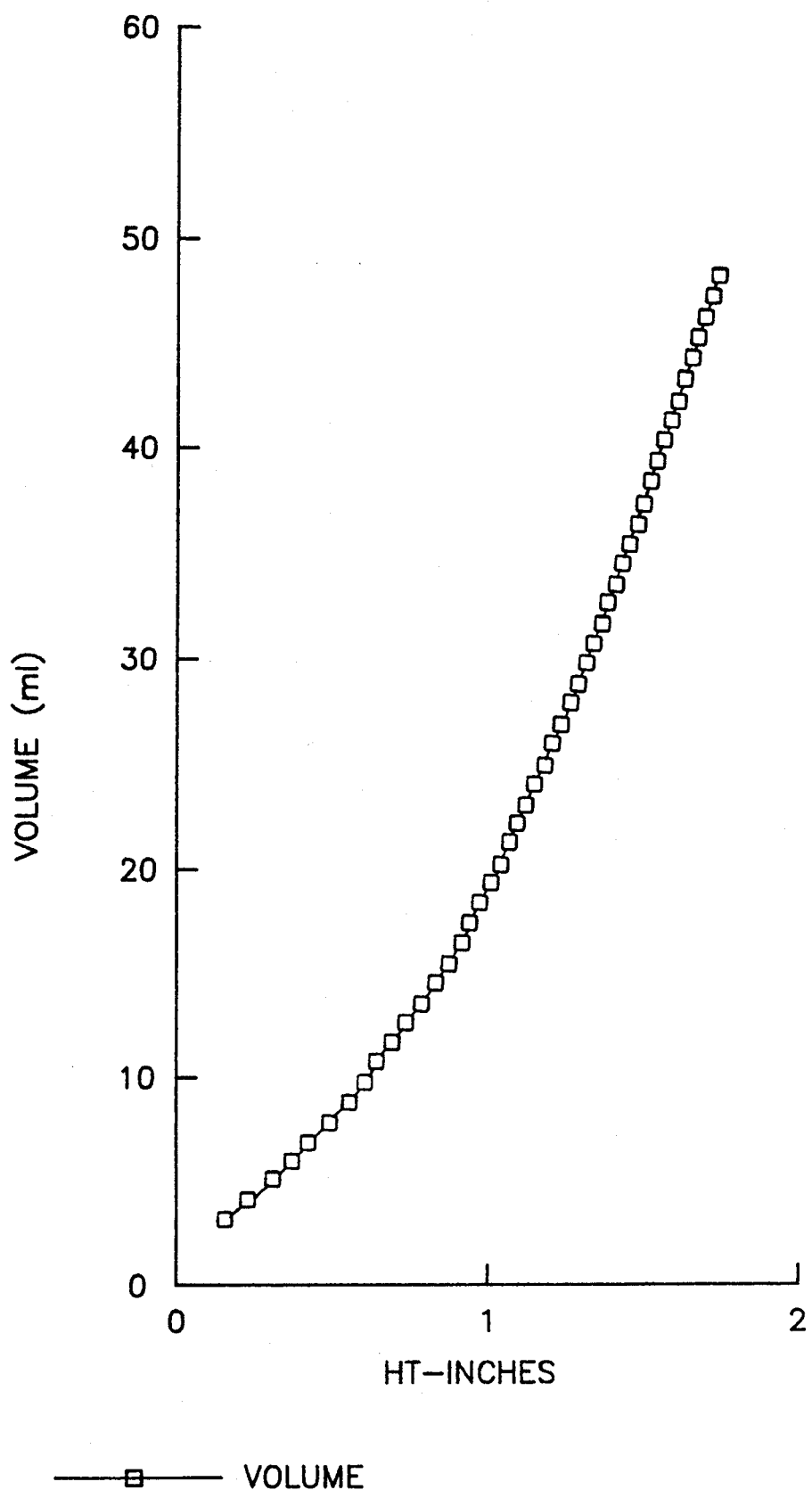
FIG. 1 is a graph depicting the increase in volume of liquid with the height in inches in the exit chamber after the pad formation screen.

What one has accomplished either by refining or polymer flocculation, has changing the surface area per unit volume. Specific filtration resistance is a strong function of this but goes beyond it in that it also depends on the use of pressure or vacuum to force liquid flow, on the size of the pad, and on the pad compressibility characteristics which relate to structure characteristics.

Accordingly, a technique has been developed to monitor specific filtration resistance or streaming potential and specific filtration resistance simultaneously in a continuous on-line manner. The method has been shown to be valid on a hardwood furnish where the specific filtration resistance and charge were varied by refining and the application of a high density low molecular weight polymer. The specific filtration resistance was compared to a maximum drainage parameter and against Schopper Reigler Freeness. All approaches track the observed trends but specific filtration resistance appears to be more sensitive. Since specific filtration resistance has a theoretical basis, it is more reliable to use it to predict drainage on the paper machine.

The principle used in the determination of streaming potential consists of drawing stock through a screen to form a pad between two electrodes; pumping white water through the pad while measuring the electrical charge as well as the pad conductance and temperature. The "assymmetry potential" represents the difference in potential between the two electrodes before and after one measurement cycle in a series. Software Subtracts out the assymmetry potential in order to present a more accurate streaming potential.

There are now several instruments which are commercially available and suitable for the measurement of streaming potential. A method and apparatus for determining streaming potential is disclosed in "Continuous measurements of the streaming Potential on a Paper Machine" by W. Sack in DAS PAPIER 30, No. 10a, pp. V42–V46 (1976). A similar method and computer controlled apparatus is described in EP 0079726B (Wiggins Teape).

More recently, an apparatus has become available which is ideally suited for the measurement of specific filtration resistance and/or the simultaneous measurement of both streaming potential and specific filtration resistance. This apparatus is described in my copending patent application Ser. No. 07/703,560, filed May 21, 1991, the entire contents of which is incorporated herein by reference.

This on-line streaming potential instrument is a well developed proven instrument which can operate continuously in a mill environment with little operator attention. As indicated above, the operating principle is that a vacuum is applied and furnish is drawn through the screen to form a pad. White water is drawn through the pad while measuring the electrical potential across the pad. This electrical potential is the streaming potential. Through use of the appropriate equations this potential can be related to the zeta potential of the fiber. The amount of water drawn through the screen and pad is monitored as a build up of height in the measuring chamber. This enables one to the volume drained as a function of time. The conductance and temperature are also monitored. All data is electronically recorded and stored in a microcomputer. The microcomputer also operates all functions of the instrument including communications with a printer and a computer which enables operator input of several parameters and output of data, or output to a Distributed Control System which can adjust chemical feed rates in order to continuously optimize the process.

Figure 8:
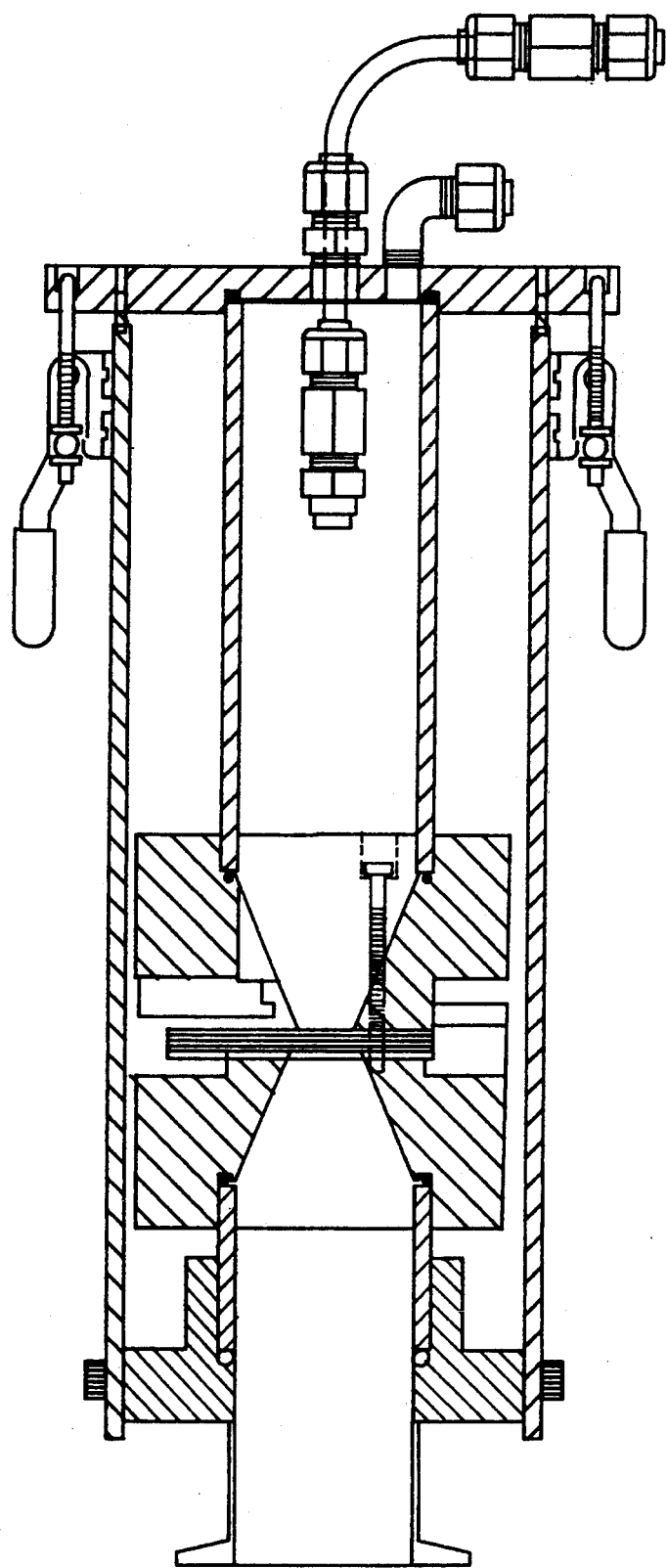
FIG. 8 is a partial cross-sectional view of a measuring cell.
Figure 9:
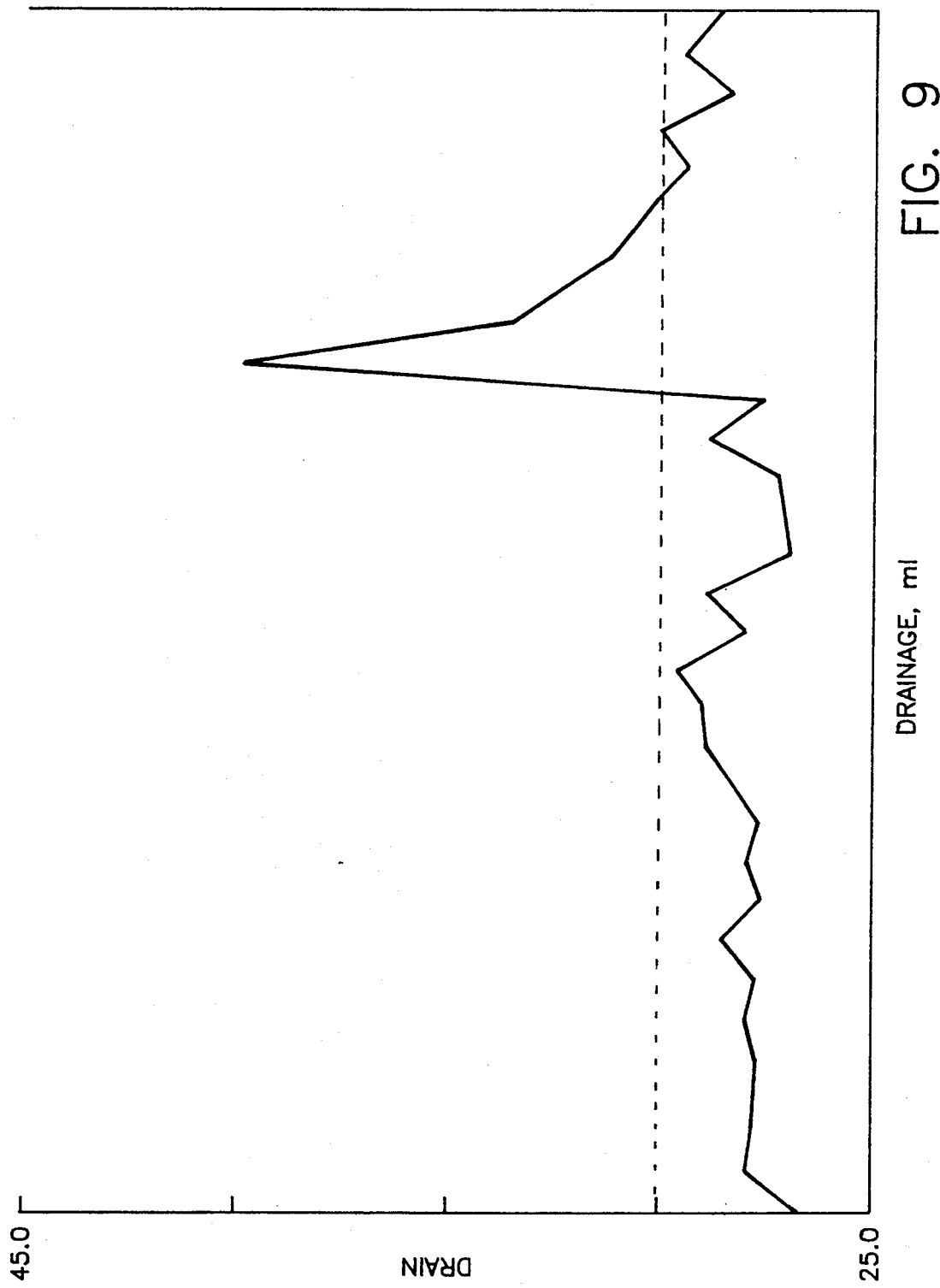
Figure 10:
Figure 12:
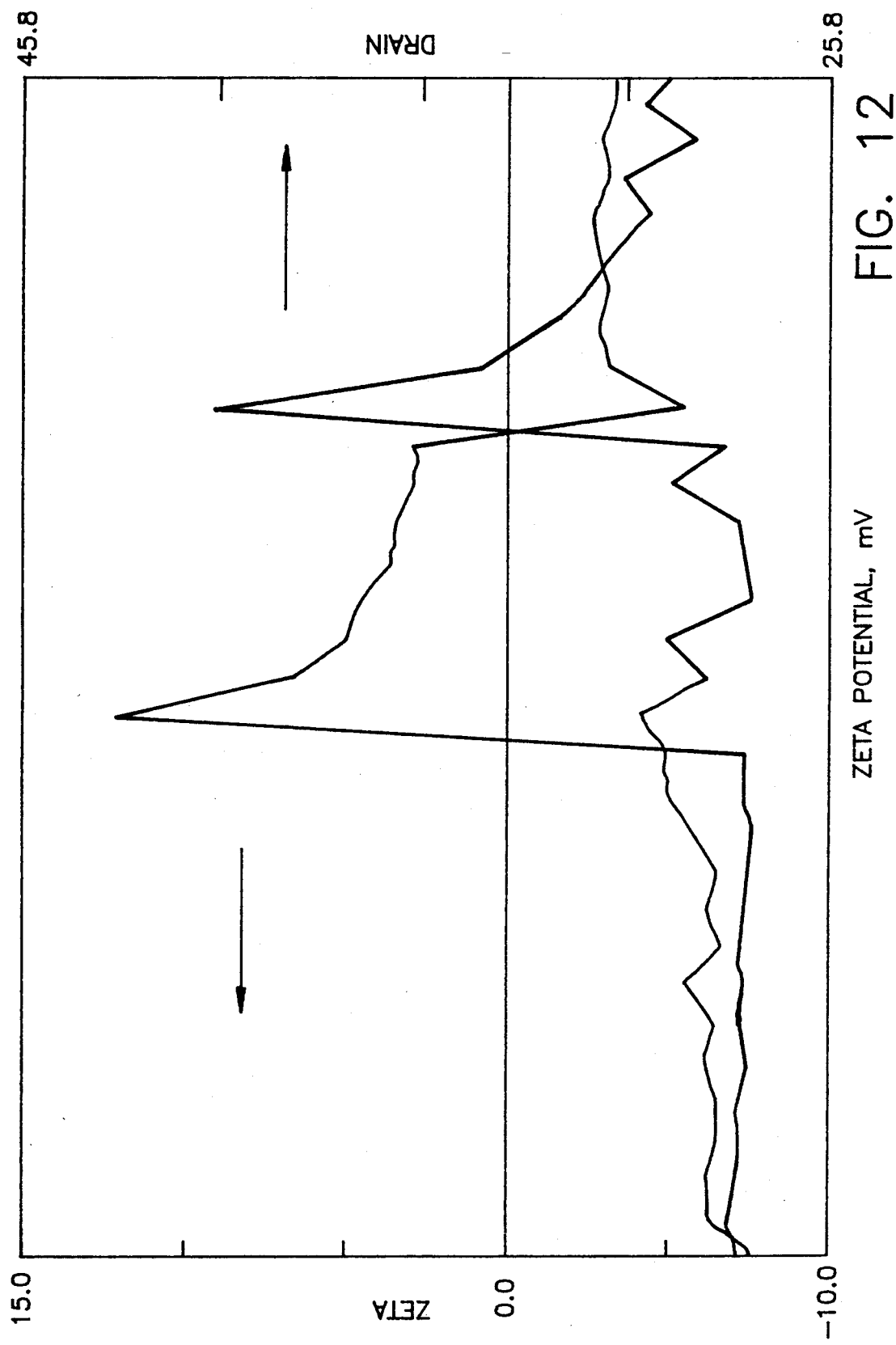

An ultrasonic transducer was added to the instrument described in the copending application together with supporting electronics so as to provide a sensor module as shown in FIG. 8 which was then used to determine the height of the liquid interface exit chamber after the pad formation screen. The height of the liquid interface was determined with an accuracy of ±0.001 inch. This height was translated into a volume drained by the correlation shown in FIG. 1. The height versus time data was automatically recorded and stored in the computer. This data was printed out and processed by software which transformed the data to volume. Measuring of the vacuum on the screen and pad sides is effected by a pressure transducer with an accuracy of ±0.001 psi. Any deviation in vacuum from the norm is corrected after each measurement and thereby contributes to the high degree of precision of the method.

Specific filtration resistance was therefore assessed by measuring the progressive increase in volume of liquid above the pad over a period of time. The lower the specific filtration resistance, the better the drainage on the paper wire machine. As indicated, the total volume of liquid which passes through the pad was measured to three digits, and expressed as "drainage in milliliters".

Table 1 below is an example of the transformation for the Shopper Riegler 50 conditions with no polymer addition.

PROCEDURE FOR SPECIFIC FILTRATION RESISTANCE

The total drainage resistance, which is a function of the flow pattern and stock composition, is the sum of the effects of resistance to the flow imposed by the wire and by the fiber mat. Thus, the filtration equation can be written:

$$dv/d\theta = AdP/[\mu(R_f + R_w)] \qquad (1)$$

where
  $dv/d\theta$ = drainage flow rate, m$^3$/s
  A = cross section of the flow, m$^2$
  dP = pressure gradient, Pa
  $\mu$ = filtrate viscosity, Pa*s
  $R_f$ = drainage resistance due to the fiber web, m$^{-1}$
  $R_w$ = drainage resistance due to the wire, m$^{-1}$ The fiber resistance, $R_f$, can be written in terms of the mass of fiber deposited on the web per unit area and a SFR coefficient:

$$R_f = (W/A)SFR \qquad (2)$$

where
  W = mass of the fiber web, kg
  A = area of the deposited fiber, m$^2$
  SFR = specific filtration resistance, m/kg For a given instant $\theta$, the mass of fiber in the web is $$W = CV\S$$

Where
  C = concentration of fibers in the slurry, kg/m$^3$
  V = volume of slurry already drained, m$^3$
  § = fraction of stock retained.

Thus, in incremental form, the combination and simplification of Eqs. 1 and 2 yields in inverted form:

$$\Delta\theta/\Delta V = \S CV(SFR)/(A^2 \Delta P) + \mu R_w/(A\Delta P) \qquad (3)$$

where
  $\Delta\theta$ = time interval to filtrate the volume
  $\Delta V$ = filtrate volume, m$^3$
  $\Delta P$ = pressure difference across the fiber mat and wire, Pa
  A = cross section of the fiber mat, m$^2$
  C = fiber concentration in the slurry, kg/m$^3$
  V = accumulated volume, m$^3$
  $\mu$ = fluid viscosity, Pa*s
  § = retention.

If Eq. 3 is valid for the flow through the fiber mat and wire, then a graph of the ratio $\Delta\theta/\Delta V$ as a function of the accumulated volume V should result in a straight line. Experiments performed during this work showed that a linear relationship can be used to describe the measured points, as assumed. The slope and the intercept of the line are used to evaluate the SFR and the wire resistance, respectively.

Implementing Procedure in Zeta Data

Figure 2:
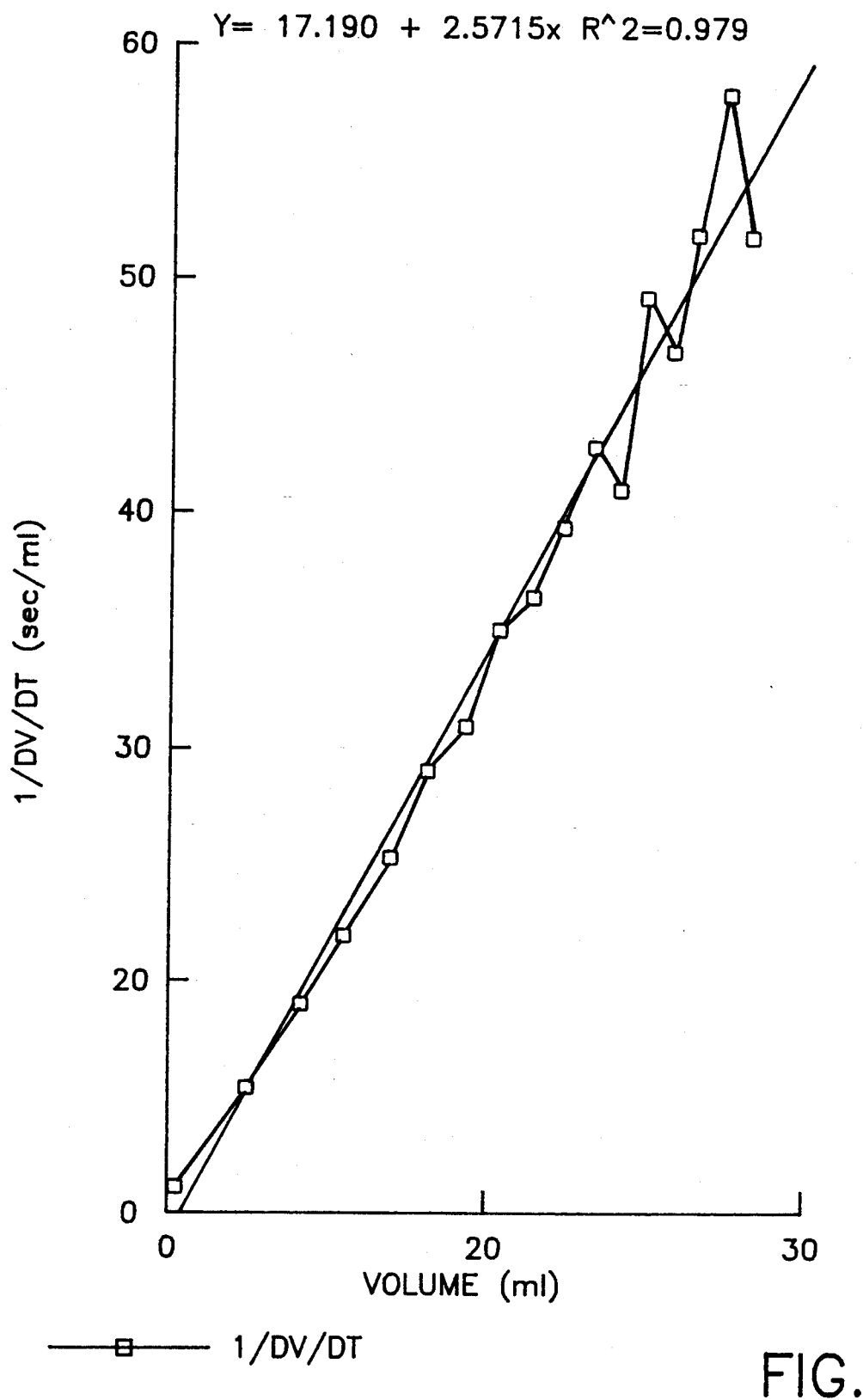
FIG. 2 is a graph depicting the least square fit to data to obtain specific filtration resistance.

A special sensor was added to the Zeta Data to determine the height of the liquid interface in the exit chamber after the pad formation screen. This height was translated into a volume drained by the correlation shown in FIG. 1. The height vs. time data was automatically recorded and stored in the computer. This data was printed out and manually processed by a software algorithm which transformed the data to volume, the change in volume and then to the reciprocal of change in volume per time. This is the transformation necessary to use the theory described under PROCEDURE FOR SPECIFIC FILTRATION RESISTANCE. Table 1 is an example of this transformation for the Shopper Riegler 50 condition with no polymer addition. This data was then plotted in appropriate form and a least squares fit line applied to the data. This is shown in FIG. 2 and is representative of most data observed in this study. The theoretical model seems to be a good fit to the data and this was found over the complete range of data collected in this study. The Specific Filtration Resistance is obtained from the slope-m.

$$SFR = \frac{mA^2\Delta P}{\mu\S C} \qquad (4)$$

A = area m$^2$
$\mu$ = viscosity PASCAL sec
C = concentration, kg/m$^3$
§ = retention
m = slope,
$\Delta P = 4.13 \times 10^4$ Pa
A = $1.266 \times 10^4$ m$^2$
C = 2 kg/m$^3$
§ = 0.8
$\mu = 6.56 \times 10^{-4}$ Pa sec.
SFR = m $\times 0.126 \times 10^{10}$ m/kg
m = 2.57 sec/ml$^2$
SFR = $6.46 \times 10^9$ m/kg Since the procedure looked good, a study was designed to see if the SFR calculated by the procedure made sense and behaved in a manner which was consistent with papermaker's knowledge of the system.

DISCUSSION OF RESULTS

Figure 3:
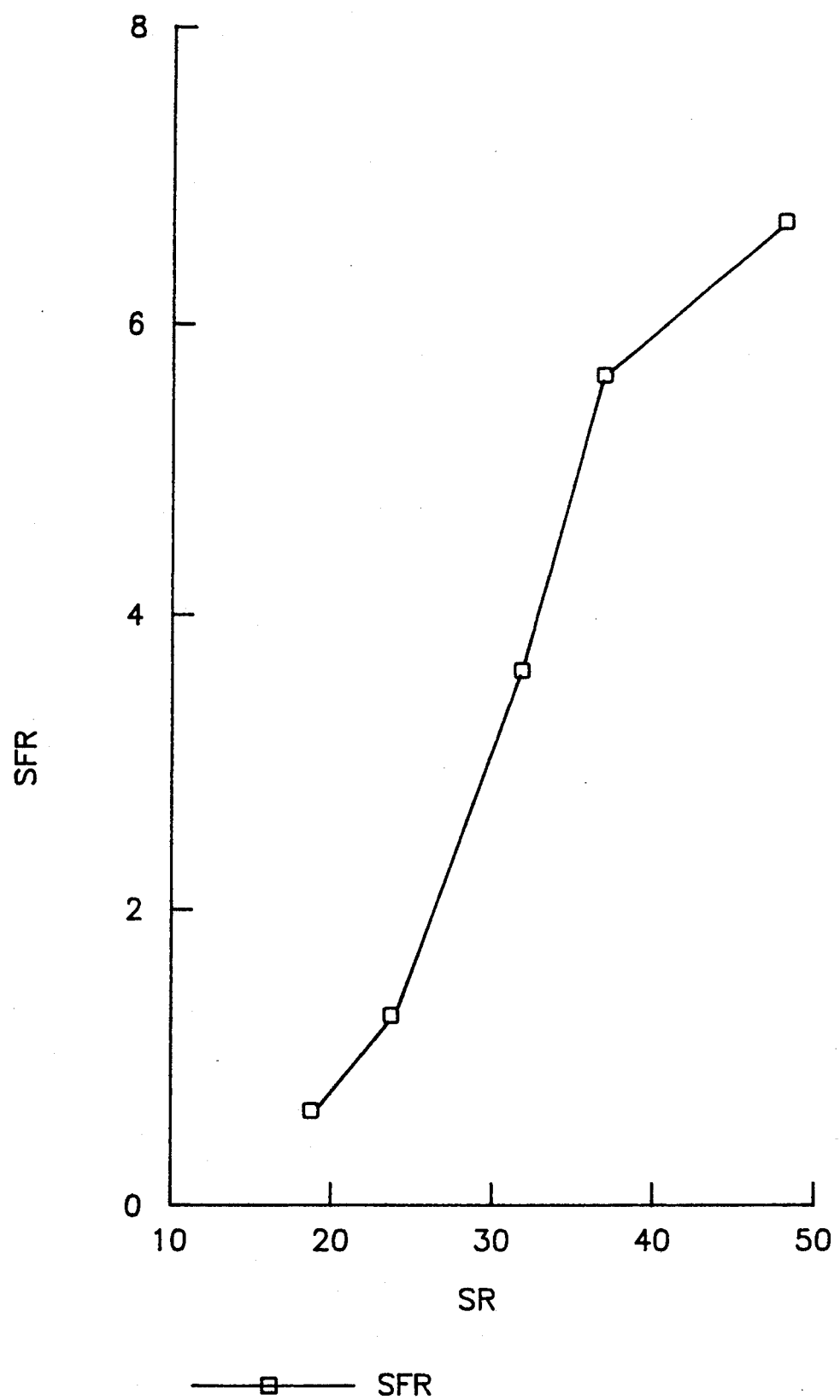
FIG. 3 is a graph showing the correlation of Schopper Reigler Freeness (SR) and specific filtration resistance (SFR).
Figure 4:
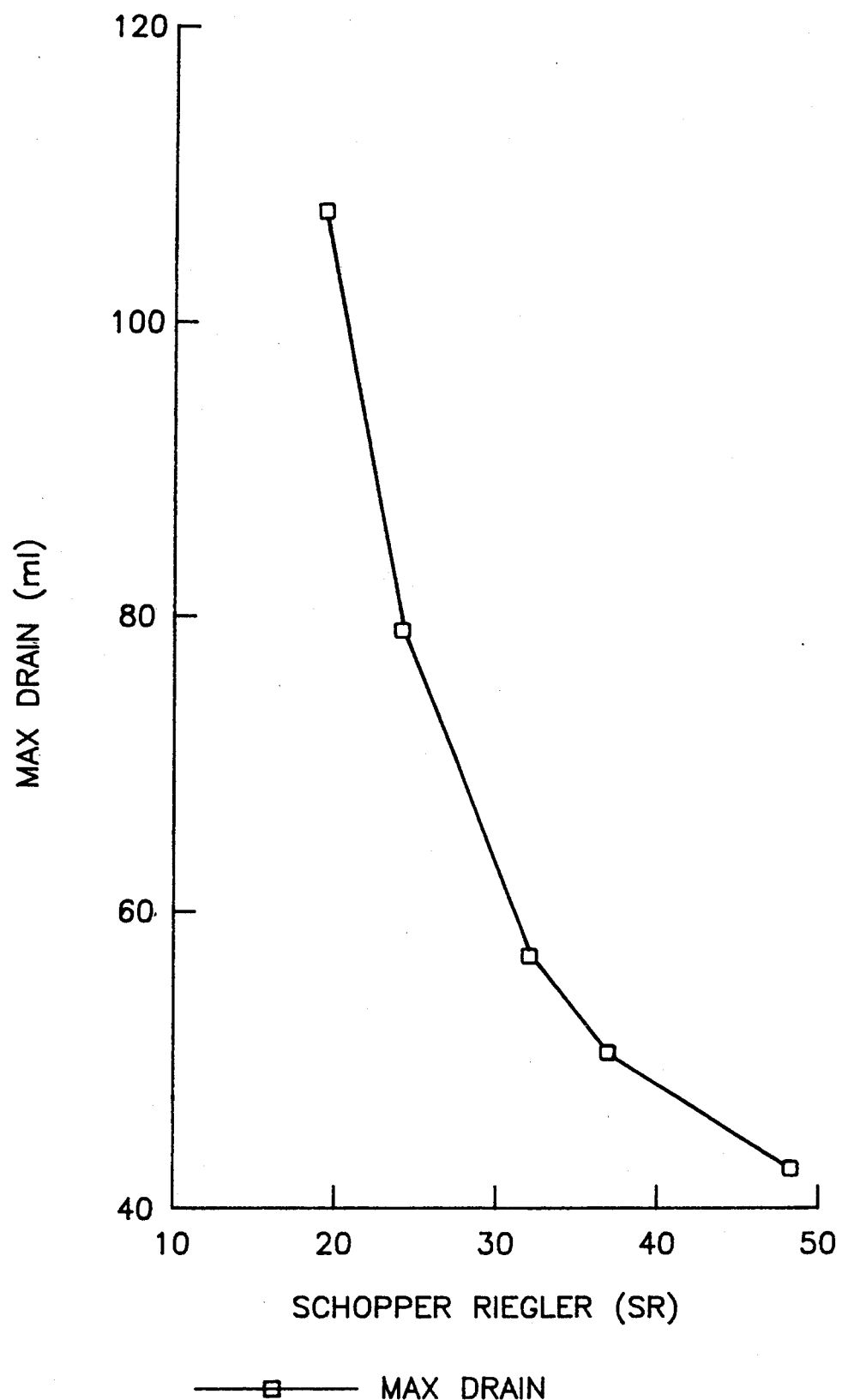
FIG. 4 is a plot showing the correlation of maximum drainage to Schopper Reigler Freeness.
Figure 5:
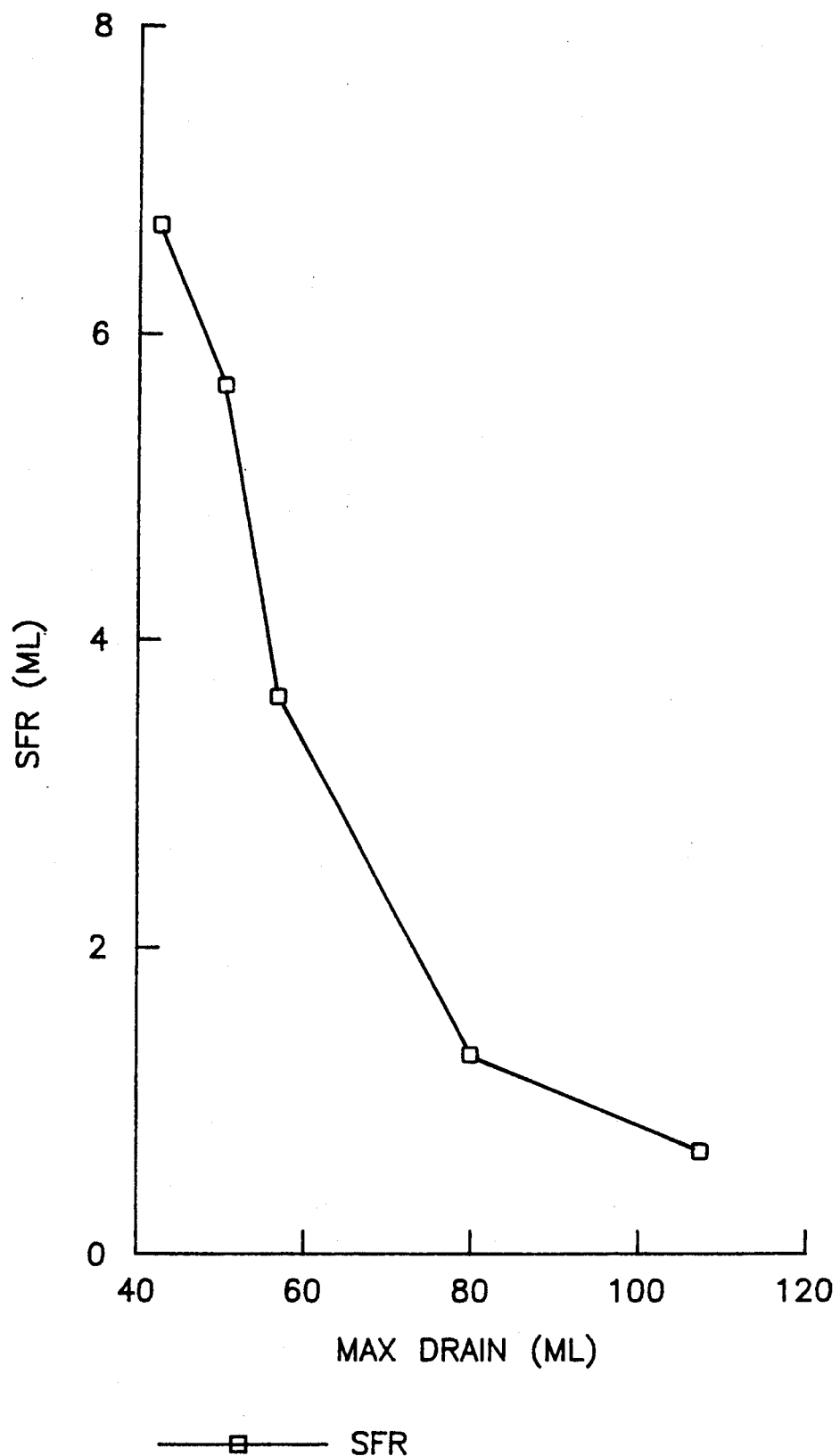
FIG. 5 is a graph depicting the correlation of specific filtration resistance and maximum drainage.

The Streaming Potential, SR, SFR and maximum drainage were determined for all samples tested. The maximum drainage is the volume drained at the end of the measurement cycle and is a quick indication of how the stock will drain. Table 2 is a summary of the results for the pure pulp samples where no polymer was added. The measurements all show the expected trend. FIG. 3 illustrates the relationship between Schopper Riegler Freeness and Specific Filtration Resistance. As expected they track each other but do not correlate to each other in a linear fashion. They are distinctly different measurements with much more useful information obtainable from SFR since it has a theoretical base. FIG. 4 shows the relationship which the maximum drainage number has with the Schopper Riegler Freeness parameter. Again they track each other but are different measurements. FIG. 5 shows the relationship of maximum drainage to Specific Filtration Resistance and again a curve results. One might think that there was Just a difference in device used to monitor, and Maximum Drainage and SFR should linearly correlate. Maximum Drainage and Schopper Riegler Freeness are merely qualitative measures of stock drainage. While they do qualitatively relate to how a stock will drain on a paper machine, they cannot quantitatively predict machine performance; only SFR has this capability. Since they are all intended to monitor the same phenomena, and they do track each other, it seems reasonable to shift to the new parameter, SFR, which has a theoretical basis.

Figure 6:
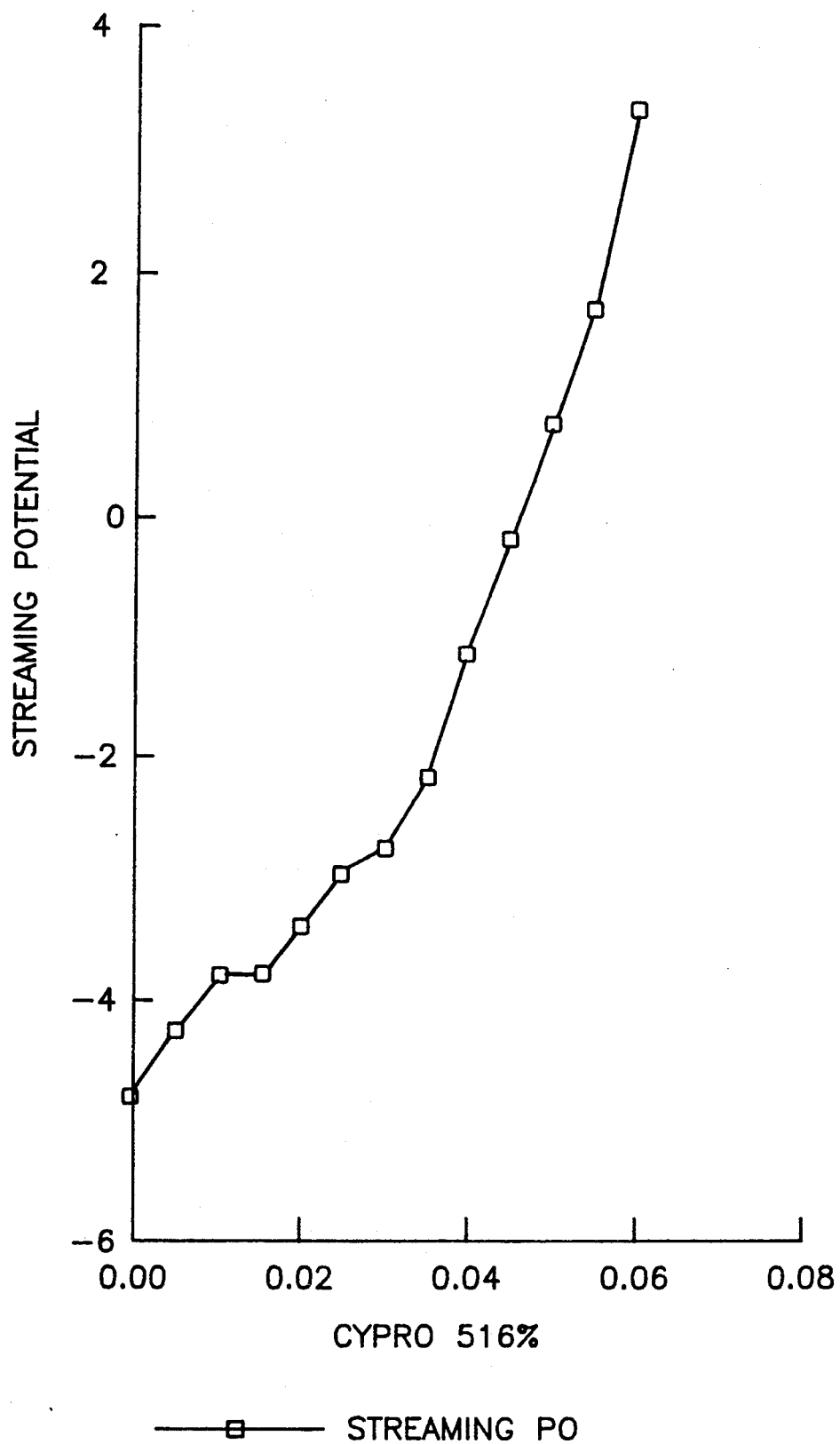
FIG. 6 depicts the influence of polymer addition on streaming potential.
Figure 7:
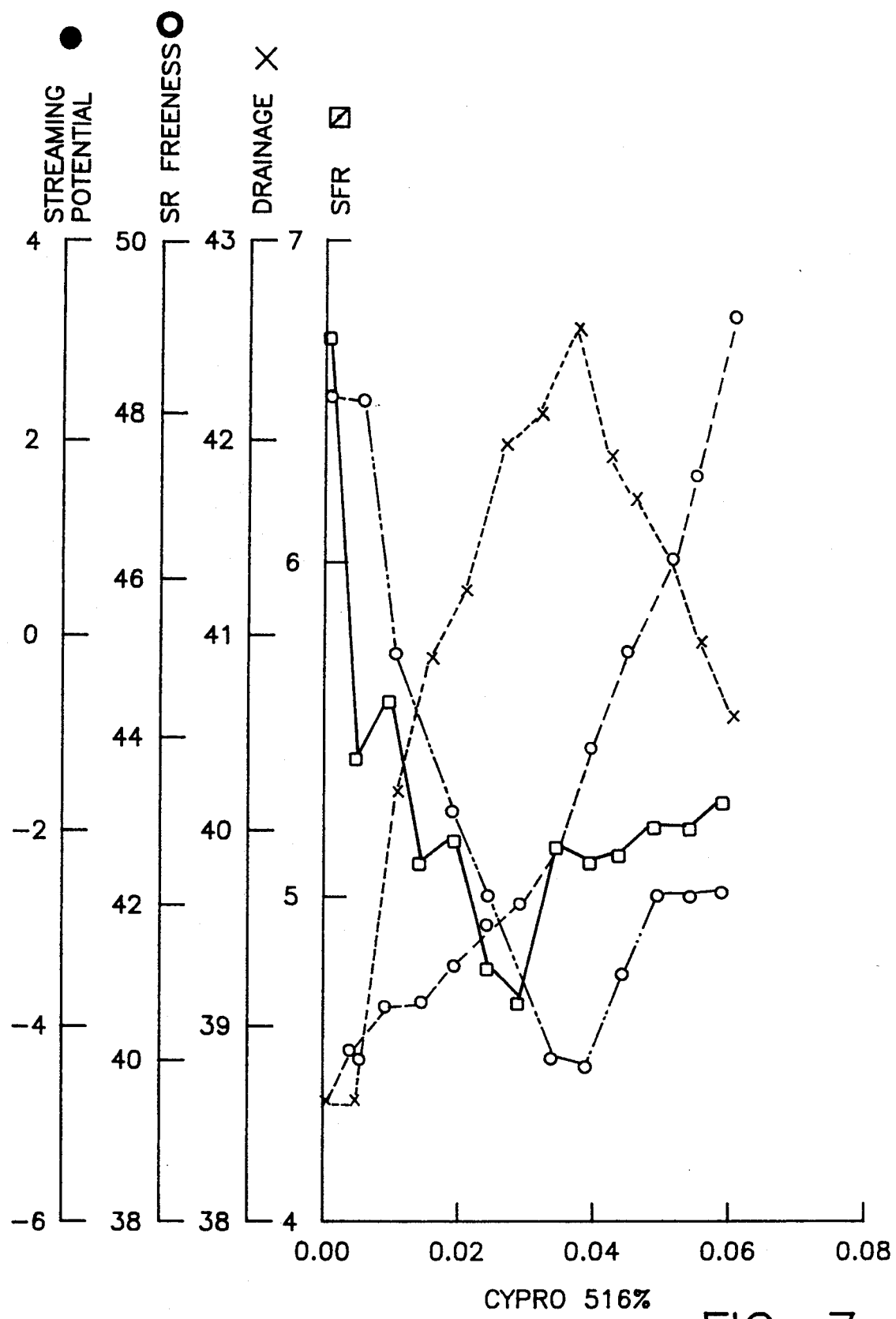
FIG. 7 is a graph showing the influence of polymer addition on drainage.

Table 3 summarizes the changes which happen to the 50 SR sample when subjected to various doses of Cypro 516. The polymer has sufficient effect on drainage to be equivalent to a shift in one level of refining chosen in this study. FIG. 6 shows the stocks' response to polymer, as far as streaming potential is concerned; the expected patterns of increase to a more positive state of charge is observed. As expected, the cationic polymer neutralizes the negative charges on the cellulose and then makes the pulp positively charged. The effect one might expect on drainage would be low drainage when the fines are dispersed, then good drainage close to the positive side zero charge. FIG. 7 shows what happens to the different drainage parameters. All three of the drainage parameters which were monitored go through an optimum. The optimum for SFR occurs before the optimum for SR freeness and Maximum Drainage. The optimum for SFR is also much more sharply defined than for SR freeness. All of the optimas occur before zero streaming potential occurs. There can be no conclusion drawn as to which measurement actually best picks optimum drainage, since the stock was not run on a machine. It appears that the minimum point for SR freeness and maximum drainage are very close so these questions will be answered when data is accumulated on machine with the Zeta Data. The patterns observed for the Maximum Drainage number are more consistent than the SR freeness patterns so the technique may be more sensitive. The SR freeness values often did not change with polymer addition and this was attributed to sensitivity.

Table 4 gives the individual SFE individual measurements taken during the polymer study. All SFE data was calculated from duplicates. The standard deviation calculated from the average range is 0.14. Thus a confidence interval for measurement of two standard deviations would be 0.28. Therefore, the procedure is reproducible and reasonably sensitive.

TABLE 1

TRANSFORMATION OF DATA FOR SR 50
(NO POLYMER CONDITION)

| | TIME | HEIGHT | VOLUME | DELTA VOL | 1/DV/DT |
|---|---|---|---|---|---|
| 1 | 1.000 | 0.117 | 3.233 | 0.233 | |
| 2 | 2.000 | 0.350 | 5.208 | 0.295 | |
| 3 | 3.000 | 0.645 | 10.350 | 0.089 | 11.236 |
| 4 | 4.000 | 0.734 | 12.481 | 0.064 | 15.625 |
| 5 | 5.000 | 0.798 | 14.179 | 0.052 | 19.231 |
| 6 | 6.000 | 0.850 | 15.662 | 0.045 | 22.222 |
| 7 | 7.000 | 0.895 | 17.019 | 0.039 | 25.641 |
| 8 | 8.000 | 0.934 | 18.250 | 0.034 | 29.412 |
| 9 | 9.000 | 0.968 | 19.366 | 0.032 | 31.250 |
| 10 | 10.000 | 1.000 | 20.452 | 0.028 | 35.714 |

TABLE 1-continued

TRANSFORMATION OF DATA FOR SR 50
(NO POLYMER CONDITION)

| | TIME | HEIGHT | VOLUME | DELTA VOL | 1/DV/DT |
|---|---|---|---|---|---|
| 11 | 11.000 | 1.028 | 21.431 | 0.027 | 37.037 |
| 12 | 12.000 | 1.055 | 22.400 | 0.025 | 40.000 |
| 13 | 13.000 | 1.080 | 23.319 | 0.023 | 43.478 |
| 14 | 14.000 | 1.103 | 24.183 | 0.024 | 41.667 |
| 15 | 15.000 | 1.127 | 25.104 | 0.020 | 50.000 |
| 16 | 16.000 | 1.147 | 25.887 | 0.021 | 47.619 |
| 17 | 17.000 | 1.168 | 26.723 | 0.019 | 52.632 |
| 18 | 18.000 | 1.187 | 27.493 | 0.017 | 58.824 |
| 19 | 19.000 | 1.204 | 28.192 | 0.019 | 52.632 |
| 20 | 20.000 | 1.223 | 28.984 | 0.096 | |
| 21 | 21.000 | 1.319 | 33.177 | | |

This data was then plotted in appropriate form and a least square fit line applied to the data. This is shown in FIG. 2 and is representative of most data observed in this study. The theoretical model is a good fit to the data. The specific filtration resistance is obtained from the slope-m.

Since the main papermaking variables which affect the way a stock drains are its degree of refining and the chemical additives introduced into the furnish, a study was designed to determine if the SFR calculated by the procedure made sense and behaved in a manner which was consistent with the paper maker's knowledge of the system. In this study plan, a bleach hardwood kraft pulp from the Champion Paper Company mill in Quinnesect, Mich., was refined from 19 SR to 48 SR with samples taken at 19, 24, 32, 37 and 48 SR. This provided a wide range of freeness over which to test the procedure. The stock samples of different freeness were then treated with Cypro 516, a high charge density low molecular weight polyquaternary amine (produced by Cytec, a Division of the American Cyanamid Corporation), dosages of 0.005% from zero to 0.06% by weight of the stock. The samples were then run through the instrument on a batch basis in a recirculating mode. The data for the no polymer condition and the data for the various polymer additions to the SR 50 stock were then evaluated.

The streaming potential, SR, SFR and maximum drainage were determined for all samples tested. The maximum drainage is the volume drained at the end of the measurement cycle and is a quick indication of how the stock will drain. Table 2 is a summary of the results for the pure pulp samples where no polymer was added. The measurements all show the expected trend.

TABLE 2

SUMMARY OF RESULTS FOR PURE PULP

| | SR | MAX DRAIN | SFR × $10^9$ | ZETA |
|---|---|---|---|---|
| 1 | 19.000 | 108.400 | 0.650 | 0.000 |
| 2 | 24.000 | 79.300 | 1.300 | 0.000 |
| 3 | 32.000 | 57.200 | 3.640 | −0.900 |
| 4 | 37.000 | 50.500 | 5.680 | −0.165 |
| 5 | 48.000 | 42.600 | 6.700 | −2.150 |

FIG. 3 illustrates the relationship between Scopper Riegler Freeness and specific filtration resistance. As expected they track each other but do not correlate to each other in a linear fashion. They are distinctly different measurements with much more useful information obtainable from SRF since it has a theoretical basis. FIG. 4 shows the relationship which the maximum drainage number has with the Schopper Riegler Freeness parameter. Again, they track each other but are different measurements. FIG. 5 shows the relationship of maximum drainage to specific filtration resistance and again a curve results. One might think that there was just a difference in the device used to monitor, and maximum drainage and SFR should correlate linearly. Schopper Riegler Freeness is merely a qualitative measure of stock drainage. While it does qualitatively relate to how a stock will drain on a paper machine, it cannot quantitatively relate to how a stock will drain on a paper machine, it cannot quantitatively predict machine performance; only SFR has this capacity. Since Schopper Riegler Freeness and SFR are both intended to monitor the same phenomena, and they do track each other, it seems reasonable to shift to the new parameter, SFR, which has a theoretical basis.

Table 3 summarizes the changes which happen to the 50 SR sample when subjected to various doses of Cypro 516. The polymer has sufficient effect on drainage to be equivalent to a shift in one level of refining chosen in this study.

TABLE 3

SUMMARY OF RESULTS FOR POLYQUATERNARY AMINE ADDITION

| | Polyquaternary amine % | SFR | Drainage | SR Freeness | Streaming Potential |
|---|---|---|---|---|---|
| 1 | 0.000 | 6.700 | 38.600 | 48.000 | −4.810 |
| 2 | 0.005 | 5.420 | 38.600 | 48.000 | −4.230 |
| 3 | 0.010 | 5.600 | 40.200 | 45.000 | −3.780 |
| 4 | 0.015 | 5.100 | 40.900 | 44.000 | −3.780 |
| 5 | 0.020 | 5.180 | 41.200 | 43.000 | −3.390 |
| 6 | 0.025 | 4.780 | 42.000 | 42.000 | −2.950 |
| 7 | 0.030 | 4.670 | 42.100 | 41.000 | −2.730 |
| 8 | 0.035 | 5.160 | 42.600 | 40.000 | −2.150 |
| 9 | 0.040 | 5.110 | 41.900 | 40.000 | −1.160 |
| 10 | 0.045 | 5.140 | 41.700 | 41.000 | −0.190 |
| 11 | 0.050 | 5.230 | 41.400 | 42.000 | 0.730 |
| 12 | 0.055 | 5.220 | 41.000 | 42.000 | 1.730 |
| 13 | 0.060 | 5.300 | 40.600 | 42.000 | 3.320 |

FIG. 6 shows the stock's response to polymer, as far as streaming potential is concerned; the expected patterns of increase to a more positive state of charge is observed. As expected, the cationic polymer neutralizes the negative charges on the cellulose and then makes the pulp positively charged. The effect one might expect on drainage would be low drainage when the fines are dispersed, then good drainage around the positive side close to zero charge. FIG. 7 shows what happens to the different drainage parameters. All three of the drainage parameters which were monitored go through an optimum. The optimum for SFR occurs before the optimum for SR freeness. The optimum for SFR is also much more sharply defined that for SR freeness. All of the optima occur before zero streaming potential occurs. There cab be no conclusion drawn as to which measurement actually best picks optimum drainage, since the stock was not run on a machine. It appears that the minimum point for SR freeness and minimum SFR are very close so this question will be answered when data is accumulated on-machine. The patterns observed for the minimum SFR number is more consistent than the SR freeness patterns so the technique may be more sensitive. The SR Freeness values often did not change with polymer addition and this was attributed to lack of sensitivity. Table 4 gives the individual SFR measurements taken during the polymer study.

TABLE 4

SR REPRODUCIBILITY

| | Polyquaternary amine % | SFR Data × $10^{-9}$ | Range | Average SFR × $10^9$ |
|---|---|---|---|---|
| 1 | 0.000 | 6.460 | | |
| 2 | | 6.940 | .48 | 6.700 |
| 3 | 0.005 | 5.380 | | |
| 4 | | 5.460 | .08 | 5.420 |
| 5 | 0.010 | 5.360 | | |
| 6 | | 5.820 | .46 | 5.600 |
| 7 | 0.015 | 5.100 | | |
| 8 | | | | 5.100 |
| 9 | 0.020 | 5.180 | | |
| 10 | | | | 5.180 |
| 11 | 0.025 | 4.760 | | |
| 12 | | 4.810 | .05 | 4.780 |
| 13 | 0.030 | 4.680 | | |
| 14 | | 4.660 | .02 | 4.670 |
| 15 | 0.035 | 5.040 | | |
| 16 | | 5.300 | .26 | 5.160 |
| 17 | 0.040 | 5.190 | | |
| 18 | | 5.040 | .15 | 5.110 |
| 19 | 0.045 | 5.090 | | |
| 20 | | 5.190 | .10 | 5.140 |
| 21 | 0.050 | 5.260 | | |
| 22 | | 5.210 | .05 | 5.230 |
| 23 | 0.055 | 5.170 | | |
| 24 | | 5.270 | .10 | 5.220 |
| 25 | 0.060 | 5.340 | | |
| 26 | | 5.260 | .08 | 5.300 |

All SFR data was calculated from duplicates. The standard deviation calculated from the average range is 0.14. Thus, a confidence interval for measurement of two standard deviations would be 0.28. Therefore, the procedure is reproducible and reasonably sensitive.

FIG. 8 is a cross-sectional view of the sensor module used for the determination of specific filtration resistance. The module is comprised of, in combination, tubing connector (1) for rinse water, tubing (2) and tubing connector (3), pneumatic tubing connector (4), O-ring (5), alignment pin (6), chamber top (7), clamp (8), tubing connector (9) for rinse nozzle connection, rinse nozzle (10), clamp support (11), chamber upper tube (12), chamber center assembly screw (13), chamber upper section (14), screen (15), electrodes (16), electrode spacer (17), drainage measuring device (18), O-ring (19), chamber base (20), clamp support mounting screw (21), clamp mounting screw (22), chamber lower tube (23) and chamber lower section (24).

In a typical experiment dry pulp was repulped in a Waring type blender in the laboratory, and adjusted to an appropriate consistency with tap water. Thirty liters of the furnish is transferred to a stainless steel vessel, equipped with an agitator. The contents of the vessel are circulated through the manifold which supplies the Sensor module of FIG. 8 with furnish.

Typically, a cationic organic chemical is added, followed after a specified delay, by an anionic inorganic microparticle. Using the system software, the zeta potential in millivolts is plotted, as is the drainage.

In a specific example, 30 liters of furnish were prepared of bleached HWD:SWD at 0.5% consistency (150 g) to which 0.125% PCC was added (37.5 g). Next, 0.25% quaternary amine (1% concentration) was added (46.9 ml). Following a ten minute delay, 1% bentonite (5% dispersion) was added (37.5 ml).

FIGS. 9, 10, 11 and 12 represent the respective printouts of the 060392B.LOG drainage and zeta potential graphs, their overlay and the logfile.

FIG. 11 shows the influence of the two additives on the zeta potential. It has been noted that the zeta potential just prior to the addition of microparticle should be slightly positive. If it is more than about +2 mV, the anionic microparticle is partly wasted in charge neutralization rather than forming a microflocculation structure, and efficiency can drop by about half. Should the charge be as negative as −5 mV prior to microparticle addition, efficiency can drop by half again. Maximizing drainage is key to the success of the microparticlate process because ensures that retention and formation are also maximized.

Figure 13:
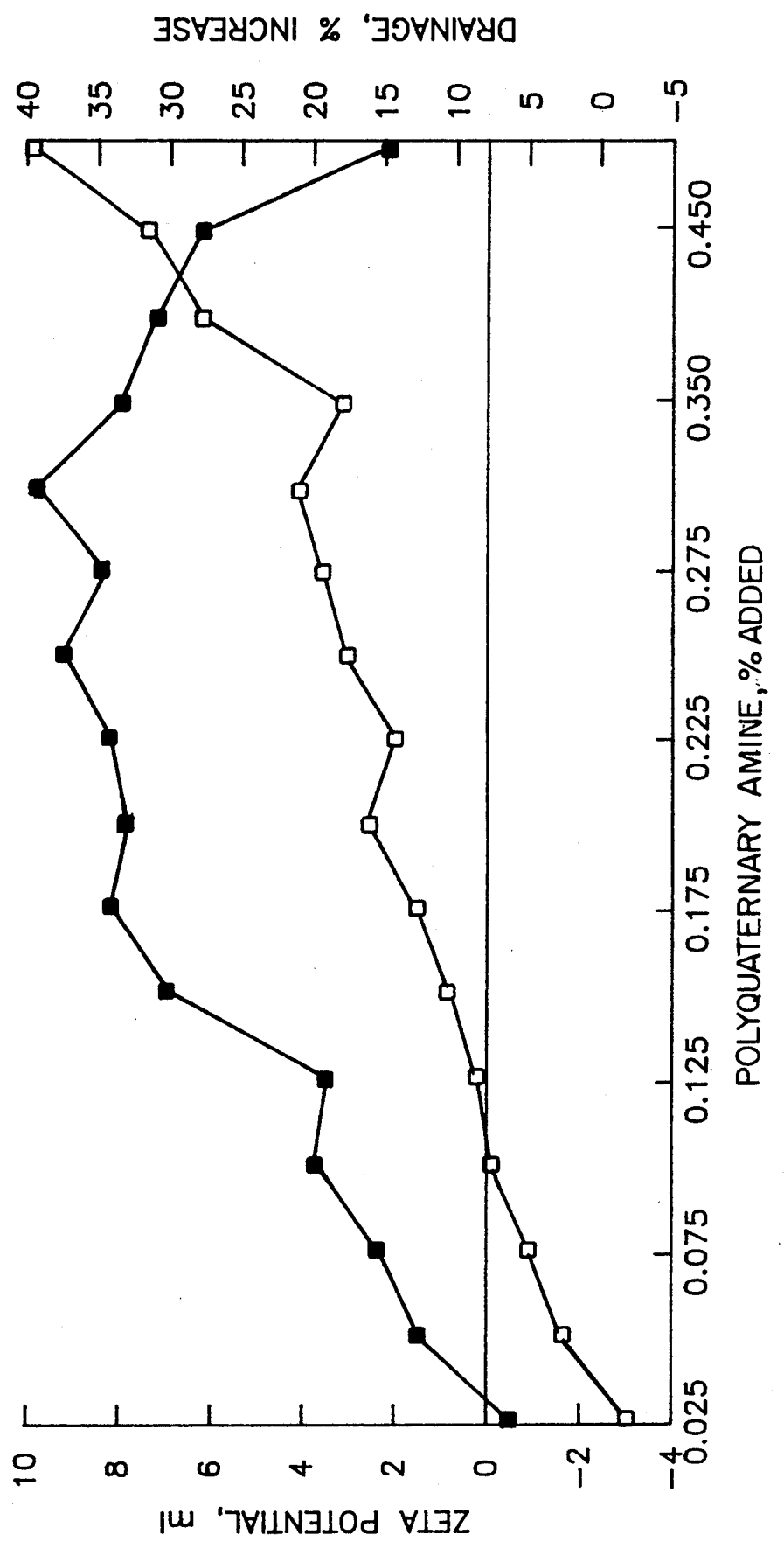
FIG. 13 is a graph depicting the influence of zeta potential on the microparticulate process.

FIG. 13, "The Influence of Zeta Potential on the Microparticulate Process" describes the incremental addition of a polyquaternary amine to an alkaline papermaking furnish, followed by the addition of an amount of colloidal silica proportional to the amount of polyquat. It is noted that in this particular case one needs to operate in the range of +2 to +4 mV zeta potential to maximize drainage. If the proportion of silica to polyquat is increased, the optimum zeta potential range becomes increasingly negative.

Figure 14:
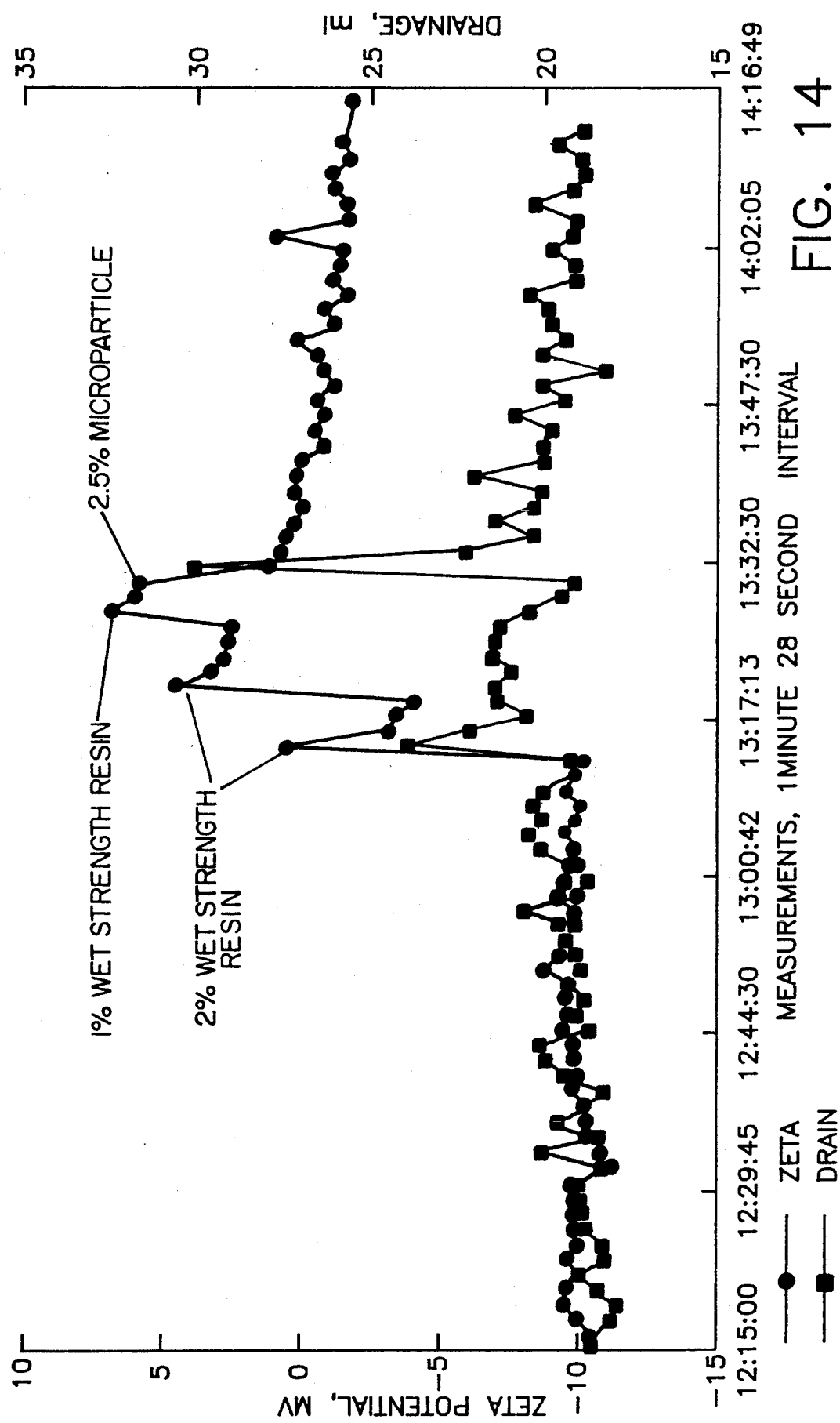
FIG. 14 is a graph showing the combined effect on zeta potential and drainage.

An investigation was also made of the effect of adding wet strength resin and a microparticle to a laminate paper furnish with 50% headbox ash, at 1% consistency. The experiment depicted four drainage states. FIG. 14 shows the combined effect on zeta potential and drainage. The first 2% increment of wet strength resin moved the zeta potential from −10 mV to 0 mV; the drainage improved from about 14 ml to 18 ml. The second 2% increment of wet strength resin moved the zeta potential; from about −4 mV to +4 mV, for a net change of zero and no change in drainage. The third 1.5% increment of wet strength resin moved the zeta potential from +2 mV to +6 mV. As the zeta potential became more positive, the drainage decreased from 22 ml to 19 ml. Finally, the microparticulate process was invoked by adding 2.5% bentonite, which caused the zeta potential to drop from +5 mV to 0 mV, causing a large increase in drainage, from 19 to 29 ml.

By the present invention there is provided a new, realistic, reproducible, continuous way to monitor specific filtration resistance.

Although the invention has been illustrated by the foregoing, it is not to be construed as being limited to the materials disclosed therein, but rather, the invention is directed to the generic area as hereinbefore disclosed. Various modifications of the invention can be made without departing from the spirit or scope thereof.

What is claimed is:

1. A method for the continuous and accurate monitoring of specific filtration resistance of a solid material in a fluid which comprises passing the fluid through a screen until a pad of the solid material is formed between two electrodes on the screen, monitoring and maintaining the pressure on the screen side of the pad with respect to the pressure on the opposing side of the pad, while measuring the height of the liquid interface on the screen side of the pad, and calculating the specific filtration resistance from the measurements taken.

2. The method of claim 1 wherein the temperature is measured.

3. The method of claim 1 wherein the solid material in the fluid is material used in paper making.

4. The method of claim 3 wherein the solid material is at least partially fibrous.

5. The method of claim 1 wherein the means of measuring the height of liquid interface uses an electronic transducer.

6. The method of claim 1 wherein the means of measuring the height of the liquid interface is accurate to ±0.001 inch.

7. The method of claim 1 wherein the means of measuring the pressure is accurate to ±0.001 psi.

8. The method of claim 6 wherein the means for measuring the pressure is a pressure transducer.

9. The method of claim 1 wherein the specific filtration resistance is calculated by a microprocessor.

10. The method of claim 1 wherein said solid material in a fluid is a furnish, and on-line adjustments are automatically made to the furnish as a result of the specific filtration resistance obtained.

11. A method for the continuous, accurate and simultaneous monitoring of streaming potential and specific filtration resistance of a solid material in a fluid which comprises passing the fluid through a screen until a pad of the solid material is formed between two electrodes on the screen, maintaining the pressure on the screen side of the pad at a predetermined value with respect to the pressure on the opposing side of the pad, measuring the temperature and conductance of the fluid while measuring the height of the liquid interface on the screen side of the pad, and calculating the zeta potential and specific filtration resistance from the measurements taken.

12. An apparatus for the continuous and accurate monitoring of specific filtration resistance of a solid material in a fluid, said apparatus comprised of, in combination, means for passing the fluid through a screen to form a pad of the solid material on the screen, pressure regulating means for measuring and maintaining the pressure on the screen side of the pad at a predetermined value with respect to the pressure on the opposing side of the pad, means for measuring the temperature and compensating for its effect; means for measuring the height of the liquid interface on the screen side of the pad and means for calculating the specific filtration resistance.

13. The apparatus of claim 12 wherein the means for measuring the height of the liquid interface uses ultrasonic measurement means.

14. The apparatus of claim 12 wherein the computation means is a microprocessor.

15. The apparatus of claim 12 wherein the means for monitoring the height of the liquid interface is accurate to 0.001 inch.

16. The apparatus of claim 12 wherein the means for monitoring the height of the liquid interface includes an ultrasonic transducer.

17. The apparatus of claim 12 wherein the means for monitoring pressure is accurate to 0.001 psi.

18. The apparatus of claim 17 wherein the means for measuring pressure is a pressure transducer.

* * * * *